(12) United States Patent
Naito et al.

(10) Patent No.: US 10,894,022 B2
(45) Date of Patent: Jan. 19, 2021

(54) METHOD FOR INCREASING AKKERMANSIA IN INTESTINAL BACTERIAL FLORA BY INGESTING ASTAXANTHIN

(71) Applicants: Fuji Chemical Industries Co., Ltd., Nakaniikawa-Gun (JP); Kyoto Prefectural Public University Corporation, Kyoto (JP)

(72) Inventors: Yuji Naito, Rittou (JP); Kazuhiro Kamada, Kyoto (JP); Kumi Tominaga, Kamiichi-Machi (JP)

(73) Assignees: Fuji Chemical Industries Co., Ltd., Nakaniikawa-Gun (JP); Kyoto Prefectural Public University Corporation, Kyoto (JP)

(*) Notice: Subject to any disclaimer, the term of this patent is extended or adjusted under 35 U.S.C. 154(b) by 0 days.

(21) Appl. No.: 15/946,783

(22) Filed: Apr. 6, 2018

(65) Prior Publication Data
US 2019/0240168 A1 Aug. 8, 2019

(30) Foreign Application Priority Data
Feb. 2, 2018 (JP) .................... 2018-017002

(51) Int. Cl.
*A61K 31/122* (2006.01)
*A61P 1/00* (2006.01)
*A61K 9/00* (2006.01)

(52) U.S. Cl.
CPC .......... *A61K 31/122* (2013.01); *A61K 9/0056* (2013.01); *A61P 1/00* (2018.01)

(58) Field of Classification Search
CPC ............. A61K 31/122; A61P 1/02; A61P 1/00
USPC ....................................................... 514/685
See application file for complete search history.

(56) References Cited

U.S. PATENT DOCUMENTS

| | | | |
|---|---|---|---|
| 6,265,450 | B1 | 7/2001 | Asami et al. |
| 6,348,347 | B1 | 2/2002 | Hirabayashi et al. |
| 2016/0199319 | A1 | 7/2016 | Yonei et al. |
| 2017/0143647 | A1 | 5/2017 | Yonei et al. |

FOREIGN PATENT DOCUMENTS

| | | |
|---|---|---|
| JP | H08-103288 A1 | 4/1996 |
| JP | H09-124470 A1 | 5/1997 |
| JP | 2007-153846 A | 6/2007 |
| WO | 99/50384 A1 | 10/1999 |
| WO | 2014/208511 A | 12/2014 |
| WO | 2015/137500 A | 9/2015 |

OTHER PUBLICATIONS

Cui et al, PLoS ONE (2017), pp. 1-18. (Year: 2017).*
AstraReal webpage, "Gastric Health," (2014). (Year: 2014).*
Derrien et al, Microbial Pathogenesis (2017), vol. 106, pp. 171-181. (Year: 2017).*
Yonei et al, Anti-Aging Medicine (2013), vol. 10 (4), pp. 77-91. (Year: 2013).*
Webpage printout of https://www.crohns.net/blog/post/irritable-bowel-syndrome-ibs, dated Jun. 14, 2017. (Year: 2017).*
Webpage printout of https://www.crohns.net/catalog/product/view/id/124/s/essential-formulas-propolis-plus-60-caps/category/178/, dated Jun. 14, 2017. (Year: 2017).*
Wei Shen, et al., "Anti-Obesity Effect of Capsaicin in Mice Fed with High-Fat Diet is Associated with an Increase in Population of the Gut Bacterium *Akkermansia muciniphila*," *Frontiers in Microbiology*, Feb. 23, 2017, vol. 8, Article 272, pp. 1-10.
Ana Maria Leal-Diaz, et al., "Aguamiel Concentrate from *Agave salmiana* and its Extracted Saponins Attenuated Obesity and Hepatic Steatosis and Increased *Akkermansia muciniphila* in C57BL6 Mice," *Scientific Reports*, Sep. 28, 2016, 6:34242, pp. 1-15.
Saeko Masumoto, et al., "Non-Absorbable Apple Procyanidins Prevent Obesity Associated with Gut Microbial and Metabolomic Changes," *Scientific Reports*, Aug. 10, 2016, 6:31208, pp. 1-10.
Fernando F. Anhe, et al., "A Polyphenol-Rich Cranberry Extract Protects from Diet-Induced Obesity, Insulin Resistance and Intestinal Inflammation in Association with Increased *Akkermansia* spp. Population in the Gut Microbiota of Mice," *Gut Microbiota*, Jun. 2015, vol. 64, pp. 872-883.
Diana E. Roopchand, et al., "Dietary Polyphenols Promote Growth of the Gut Bacterium *Akkermansia muciniphila* and Attenuate High-Fat Diet-Induced Metabolic Syndrome," *Diabetes*, vol. 64, Aug. 2015, pp. 2847-2858.
Xichun Peng, et al., "In Vitro Catabolism of Quercetin by Human Fecal Bacteria and the Antioxidant Capacity of its Catabolites," *Food and Nutrition*, Apr. 2014, 15:58, pp. 1-7.
Norihisa Noguchi, et al., "Association of Tannase-Producing *Staphylococcus lugdunensis* with Colon Cancer and Characterization of a Novel Tannase Gene," *J. Gastroenterol*, May 2007, vol. 42, pp. 346-351.
Kalil et. al., "Brazilian Green Propolis as a Therapeutic Agent for the Post-surgical Treatment of Caseous Lymphadenitis in Sheep," *Frontiers in Veterinary Science*, dated Nov. 26, 2019 | https://doi.org/10.3389/fvets.2019.00399 (10 pages).

* cited by examiner

*Primary Examiner* — Craig D Ricci
*Assistant Examiner* — Janet L. Coppins
(74) *Attorney, Agent, or Firm* — Burr & Brown, PLLC

(57) ABSTRACT

A method for increasing bacteria belonging to the genus *Akkermansia* in an intestinal bacterial flora, comprising the step of ingesting a composition containing astaxanthin.

5 Claims, 4 Drawing Sheets

FIG. 2A

| DIET | TREAT-MENT | PARENT NUMBER | ANIMAL NUMBER | NUMBER OF FECES | BODY WEIGHT | | | Δ |
|---|---|---|---|---|---|---|---|---|
| | | | | | PND24 | PND35 | PND72,76 | PND72,76-24 |
| control | saline | ⑥ | 6-1 | 0 | 75.7 | 160.1 | 397.3 | 321.6 |
| | | ⑥ | 6-2 | 0 | 82.0 | 164.5 | 414.8 | 332.8 |
| | | ⑥ | 6-3 | 0 | 80.8 | 166.0 | 420.8 | 340 |
| | | ⑧ | 8-1 | 7 | 89.3 | 184.9 | 480.6 | 391.3 |
| | | ⑨ | 9-4 | 3 | 83.8 | 185.4 | 463.5 | 379.7 |
| | | ⑨ | 9-5 | 2 | 87.1 | 187.8 | 478.5 | 391.4 |
| | CRH | ⑥ | 6-4 | 3 | 77.7 | 162.8 | 443.8 | 366.1 |
| | | ⑥ | 6-5 | 5 | 82.0 | 173.2 | 438.4 | 356.4 |
| | | ⑦ | 7-4 | 9(2) | 74.2 | 164.1 | 397.0 | 322.8 |
| | | ⑦ | 7-5 | 3 | 70.9 | 158.0 | 395.9 | 325 |
| | | ⑧ | 8-2 | 0 | 85.3 | 179.3 | 355.0 | 269.7 |
| | | ⑨ | 9-6 | 8 | 81.5 | 174.7 | 450.4 | 368.9 |
| | | ⑨ | 9-7 | 11 | 81.3 | 182.9 | 462.7 | 381.4 |
| Asx | saline | ⑩ | 10-1 | 2 | 75.0 | 165.1 | 403.4 | 328.4 |
| | | ⑩ | 10-2 | 0 | 76.8 | 163.0 | 407.3 | 330.5 |
| | | ⑩ | 10-3 | 0 | 74.3 | 161.6 | 390.3 | 316 |
| | | ⑩ | 10-4 | 1 | 74.2 | 166.5 | 418.5 | 344.3 |
| | | ⑩ | 10-7 | 0 | 81.1 | 165.1 | 392.6 | 311.5 |
| | | ⑩ | 10-8 | 3 | 77.4 | 165.6 | 419.7 | 342.3 |
| | CRH | ⑦ | 7-1 | 0 | 73.2 | 161.4 | 360.6 | 287.4 |
| | | ⑦ | 7-2 | 5(1) | 73.8 | 163.3 | 470.1 | 396.3 |
| | | ⑦ | 7-3 | 0 | 71.6 | 165.5 | 447.3 | 375.7 |
| | | ⑨ | 9-1 | 0 | 82.3 | 163.1 | 351.6 | 269.3 |
| | | ⑨ | 9-2 | 2 | 80.9 | 170.7 | 389.6 | 308.7 |
| | | ⑨ | 9-3 | 3 | 83.4 | 174.4 | 390.5 | 307.1 |
| | | ⑩ | 10-5 | 4(1) | 81.2 | 177.3 | 406.4 | 325.2 |
| | | ⑩ | 10-6 | 4 | 74.1 | 166.6 | 424.8 | 350.7 |

Asx: A DIET CONTAINING ASTAXANTHIN
CRH: INTRAVENOUS ADMINISTRATION OF 10 μg OF CRH

FIG. 2B

| | Avg. PND72,76 | Avg. INCREASE |
|---|---|---|
| Control | 430.7 | 349.8 |
| Ax | 405.2 | 328.1 |

| | DURATION OF INGESTION OF ASTAXANTHIN (DAYS) | | | | | | | |
|---|---|---|---|---|---|---|---|---|
| INDIVIDUAL NO. | 0 | 1 | 6 | 13 | 20 | 27 | 34 | 42 |
| 1 | 13.3 | 54.7 | 199.5 | 152.6 | 115.3 | 33.9 | 68.5 | 101.2 |
| 2 | 29.5 | 134.6 | 251.5 | 256.8 | 207.1 | 220.6 | 229.5 | 240.4 |
| 3 | 37.2 | 31.4 | 264.0 | 385.5 | 190.8 | 319.6 | 365.9 | 272.4 |
| 4 | 21.6 | 58.4 | 93.2 | 142.1 | 121.9 | 102.1 | 108.6 | 146.6 |
| 5 | 13.6 | 123.2 | 219.3 | 206.2 | 248.4 | 270.3 | 292.1 | 241.3 |
| 6 | 24.9 | 114.3 | 68.8 | 166.4 | 118.3 | 141.1 | 148.7 | 153.1 |
| 7 | 20.1 | 116.2 | 256.3 | 201.9 | 235.6 | 108.9 | 143.8 | 212.7 |
| 8 | 31.4 | 101.6 | 152.8 | 198.5 | 252.4 | 236.7 | 231.1 | 220.1 |
| 9 | 24.4 | 138.4 | 233.3 | 277.2 | 188.0 | 275.5 | 232.3 | 329.2 |
| 10 | 39.0 | 115.7 | 210.3 | 270.2 | 257.0 | 215.2 | 179.7 | 179.0 |
| AVERAGE | 25.5 | 98.8 | 194.9 | 225.7 | 193.5 | 192.4 | 200.0 | 209.6 |
| SD | 8.9 | 37.1 | 68.4 | 73.5 | 57.2 | 91.5 | 88.7 | 66.8 |

METHOD FOR INCREASING AKKERMANSIA IN INTESTINAL BACTERIAL FLORA BY INGESTING ASTAXANTHIN

Japanese Patent Application No. 2018-17002 filed on Feb. 2, 2018, is hereby incorporated by reference in its entirety.

BACKGROUND

The present invention relates to a method for improving bacteria belonging to the genus *Akkermansia* in an intestinal bacterial flora, and the like.

The intestinal bacterial flora changes depending on factors such as living environment and is believed to have a great impact on, for example, health status.

For example, irritable bowel syndrome (IBS) is a gastrointestinal dysfunction in which a symptom such as diarrhea, constipation, and abdominal pain occurs although no organic abnormalities such as inflammation and ulcer are found by an examination, and is considered to be a type of functional dyspepsia.

Although the pathogenic mechanism of IBS is still unknown in many respects, attention has been drawn to correlation between central nervous function and gastrointestinal function, specifically, gut-brain interaction and hypersensitive gastrointestinal tract in the context of psychological stress.

Some enterobacteria greatly influence obesity and a disease associated therewith.

As is detailed below, it is reported that *Akkermansia muciniphila* enterobacteria are associated with obesity and a disease associated therewith.

The present inventors investigated how astaxanthin influenced the intestinal bacterial flora and consequently accomplished the present invention.

Japanese Patent Laid-Open No. H09-124470 discloses an anti-stress composition containing astaxanthin and/or an ester thereof as an active ingredient; however it does not disclose the influence of the composition on the intestinal bacterial flora in any way.

SUMMARY

A feature of an aspect of the present invention is inclusion of a step of ingesting a composition containing astaxanthin.

According to this feature, it is possible to increase bacteria belonging to the genus *Akkermansia* in an intestinal bacterial flora

BRIEF DESCRIPTION OF THE DRAWINGS

FIGS. 2A and 2B show the result of a comparative study of increases in body weight;

DESCRIPTION OF EXEMPLARY EMBODIMENTS

Figure 1:
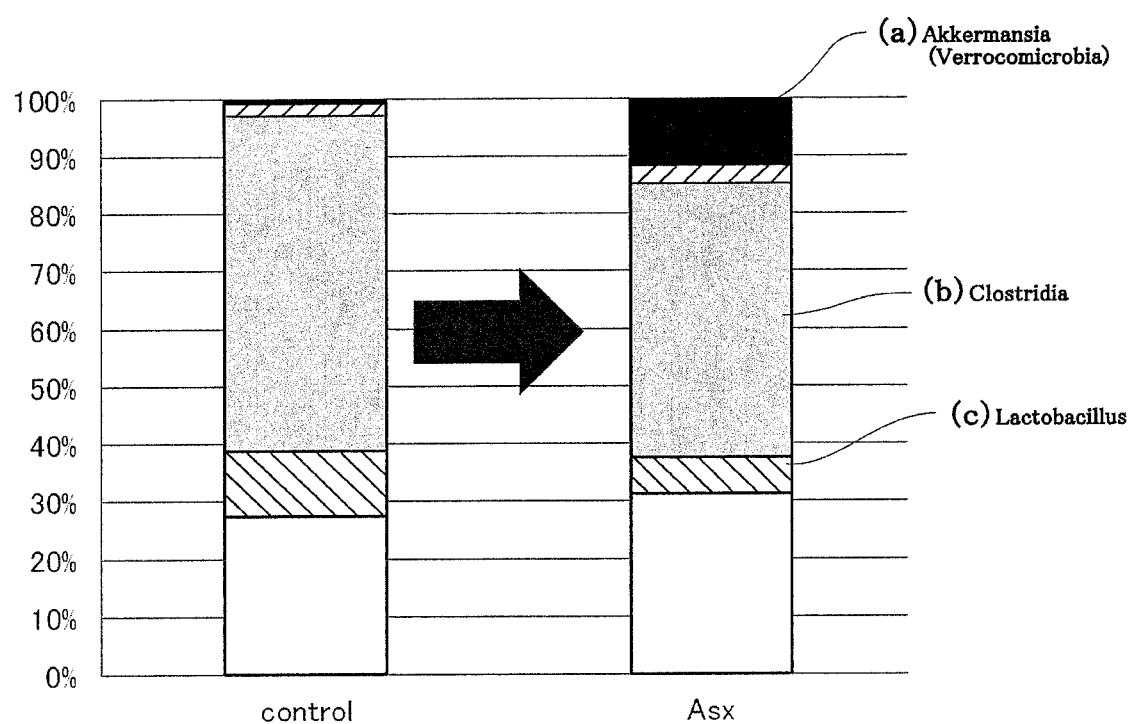
FIG. 1 shows the result of comparison of intestinal bacterial floras.

It is an object of the present invention to improve the balance of an intestinal bacterial flora, in particular, to increase bacteria belonging to the genus *Akkermansia*.

An embodiment of the present invention includes the step of ingesting a composition containing astaxanthin for increasing bacteria belonging to the genus *Akkermansia* in the intestinal bacterial flora, preferably *Akkermansia muciniphila* among others.

Astaxanthin is a type of carotenoid. Carotenoids are classified into carotenes and xanthophylls, and astaxanthin belongs to the xanthophyll group.

The IUPAC name of astaxanthin is 3,3'-dihydroxy-$\beta,\beta$-carotene-4,4'-dione and there are three forms of astaxanthin depending on the configurations of the hydroxy groups at 3 and 3' positions: a (3R,3'R) form, a (3R,3'S) form, and a (3S,3'S) form.

Astaxanthin also has isomers defined by a cis-trans orientation around a conjugated double bond, and exists in a free form, a monoesterified form, or a diesterified form.

Astaxanthin is known to have an antioxidative activity and it has low absorption efficiency, with its absorption percentage in the intestine being about 5%.

It is presumed from this fact that about 95% of astaxanthin is not absorbed and remains in the intestine, and directly acts on the intestinal bacterial flora.

Thus, as detailed below, 6-week-old Wistar rats (rodents) were used to compare the intestinal bacterial floras of a group fed with an astaxanthin-containing diet for four weeks and a group fed with a normal diet for four weeks. It is presumed from the result that the number of *Akkermansia muciniphila*, bacteria of the genus *Akkermansia*, in the group fed with the astaxanthin-containing diet increased and is about 11.7 times higher than that of the group fed with the normal diet.

Articles reported so far were reviewed and polyphenols such as Capsaicin (Shen W, Shen M, Zhao X, Zhu H, Yang Y, Lu S, Tan Y, Li G, Li M, Wang J, Hu F, Le S. "Anti-obesity Effect of Capsaicin in Mice Fed with High-Fat Diet Is Associated with an Increase in Population of the Gut Bacterium *Akkermansia muciniphila*." Front Microbiol. 2017 Feb. 23; 8), saponin (Leal-Diaz A M, Noriega L G, Torre-Villalvazo I, Torres N, Aleman-Escondrillas G, Lopez-Romero P, Sanchez-Tapia M, Aguilar-Lopez M, Furuzawa-Carballeda J, Velazquez-Villegas L A, Avila-Nava A, Ordaz G, Gutierrez-Uribe J A, Serna-Saldivar S O, Tovar A R. "Aguamie concentrate from Agave salmiana and its extracted saponins attenuated obesity and hepatic steatosis and increased *Akkermansia muciniphila* in C57BL6 mice." Sci Rep. 2016 Sep. 28; 6:34242), Procyanidin (Masumoto S, Terao A, Yamamoto Y, Mukai T, Miura T, Shoji T. "Non-absorbable apple procyanidins prevent obesity associated with gut microbial and metabolomic changes." Sci Rep. 2016 Aug. 10; 6:31208), Cranberry extract (Anhe F F, Roy D, Pilon G, Dudonne S, Matamoros S, Varin T V, Garofalo C, Moine Q, Desjardins Y, Levy E, Marette A. "A polyphenol-rich cranberry extract protects from diet-induced obesity, insulin resistance and intestinal inflammation in association with increased *Akkermansia* spp. population in the gut microbiota of mice." Gut. 2015 June; 64(6):872-83), Concord grape (Roopchand D E, Carmody R N, Kuhn P, Moskal K, Rojas-Silva P, Turnbaugh P J, Raskin I. "Dietary Polyphenols Promote Growth of the Gut Bacterium *Akkermansia muciniphila* and Attenuate High-Fat Diet-Induced Metabolic Syndrome." Diabetes. 2015 August; 64(8):2847-58) had been reported to show an effect of increasing *Akkermansia muciniphila*. However, polyphenol is reported to be degraded by enterobacteria, and therefore is disadvantageous for improvement of the intestinal bacterial flora and safety (Peng X, Zhang Z, Zhang N, Li S, Wei H. "In vitro catabolism of quercetin by human fecal bacteria and the antioxidant capacity of its catabolites." Food Nutr Res. 2014 Apr. 15; 58, Noguchi N, Ohashi T, Shiratori T, Narui K, Hagiwara T, Ko M, Watanabe K, Miyahara T, Taira S, Moriyasu F, Sasatsu M. "Association of tannase-producing *Staphylococcus lugdunensis* with colon cancer and characterization of a novel tannase gene." J Gastroenterol. 2007 May; 42(5):346-51).

A fecal microbiota transplantation method, by which fecal matter from a person carrying *Akkermansia muciniphila* in the body is transplanted, is another possible method for increasing *Akkermansia muciniphila*; however, the effectiveness of this method varies among individuals and moreover this method is not practical in terms of cost.

The below-mentioned study result indicated that the range of blood astaxanthin concentrations in the rodents was 0 to 1720 ng/ml (excluding 0), preferably 0 to 820 ng/ml (excluding 0), and more preferably 0 to 55 ng/ml (excluding 0).

It is preferable that a human ingests 1 to 40 mg of astaxanthin per day for achieving the above-mentioned more preferable blood concentration.

When a human ingested 1 to 60 mg of astaxanthin per day, the range of its blood concentration was more than 0 and no more than 600 ng/ml.

Astaxanthin that may be used in an embodiment of the present invention is not particularly limited and at least one of natural astaxanthin and synthetic astaxanthin may be used.

Examples of the natural astaxanthin may include astaxanthin obtainable from an alga such as a *Haematococcus* alga; a yeast such as a Phaffia yeast; a crustacean such as a shrimp, a krill, and a crab; a cephalopod such as a squid and an octopus; various fishes and shellfishes; a plant such as an *Adonis* plant; a bacterium such as *Paracoccus* sp. N81106, *Brevundimonas* sp. SD212, and Erythrobacter sp. PC6; an actinomycete such as *Gordonia* sp. KANMONKAZ-1129; a Labyrinthulomycetes such as Schizochytrium sp. KH105; and an organism genetically modified to produce astaxanthin. A preferable example may be astaxanthin extracted from a microalga such as a *Haematococcus* alga and a more preferable example may be astaxanthin extracted from a *Haematococcus* alga. Examples of the synthetic astaxanthin may include AstaSana (DSM) and Lucantin Pink (R) (BASF). Examples of the synthetic astaxanthin chemically converted from other naturally-occurring carotenoids may include AstaMarine (PIVEG, Inc.).

Examples of the *Haematococcus* alga from which natural astaxanthin is obtainable may include *Haematococcus pluvialis, Haematococcus lacustris, Haematococcus capensis, Haematococcus droebakensis*, and *Haematococcus zimbabwiensis*.

A preferable method for culturing these *Haematococcus* algae is a culture method in an enclosed system, in which no contamination or growth of a different species of microorganism occurs and a low level of contamination by other foreign substances occurs. Examples of such a culture method may include a culture method by using a culture apparatus including a partially-open-type culture device in a domed, conical, or cylindrical shape and a gas jet unit freely movable within the device (International Publication No. WO 1999/050384); and a method including the steps of inducing encystment of a *Haematococcus* alga by applying drying-stress to it and collecting astaxanthin from the culture of the encysted *Haematococcus* alga (Japanese Patent Laid-Open No. H08-103288); a culture method by using an enclosed culture device with a light source placed therein, the light source emitting light internally; and a method by using a tabular fermenter or a tubular fermenter.

Astaxanthin and/or the composition containing astaxanthin that can be used in an embodiment of the present invention may be, for example, astaxanthin obtained by crushing cell walls of the above-mentioned *Haematococcus* alga, if required, according to a method disclosed in, for example, Japanese Patent Laid-Open No. H05-068585; adding a solvent such as an organic solvent, for example, acetone, an ether, chloroform, and an alcohol (e.g., ethanol and methanol) and supercritical carbon dioxide; and performing extraction, and/or a composition containing such astaxanthin. In this case, the astaxanthin concentration in the composition containing astaxanthin is preferably 3 to 40% (w/w), more preferably 3 to 12% (w/w), and even more preferably 5 to 10% (w/w).

Furthermore, examples of astaxanthin and/or the composition containing astaxanthin that can be used in an embodiment of the present invention can include a commercially available product. Examples of such a commercially available product may include the ASTOTS series such as ASTOTS-S, ASTOTS-100, ASTOTS-ECS, ASTPTS-2.0PW, and ASTOTS-3.0 MB (In all products, ASTOTS is a registered trademark. Fujifilm Corporation); the AstaReal, Astavita, and Astamate series, such as AstaReal oil 50F, AstaReal oil 5F, AstaReal powder 20F, water-soluble AstaReal solution, AstaReal WS solution, AstaReal 10WS solution, AstaReal ACT, Astavita e, Astavita SPORTS, and Astamate (all are registered trademarks. AstaReal Co., Ltd., Fuji Chemical Industry Co, Ltd.); BioAstin ((R), Cyanotech Corporation); Astazine™ (BGG Japan Co., Ltd.); astaxanthin powder 1.5%, astaxanthin powder 2.5%, astaxanthin oil 5%, astaxanthin oil 10% (Bio Actives Japan Corporation); astaxanthin (Oryza Oil&Fat Chemical Co., Ltd.); SunActive AX (R) (Taiyo Kagaku Co., Ltd.); *Haematococcus* WS30 (YAEGAKI Bio-industry, Inc.); and AstaMarine (Piveg, Inc.).

A method for ingesting astaxanthin may be by consuming a supplement, a health food, a functional nutritional food, or the like, or a beverage supplemented with astaxanthin. Furthermore, another method for ingesting astaxanthin may be by administering astaxanthin as various pharmaceutical compositions such as a tablet, a capsule, a granule, a fine granule, and a liquid formulation.

Advantageous Effects of Invention

Ingestion of the composition containing astaxanthin as described above leads to increase of *Akkermansia (muciniphila)* in the intestinal bacterial flora and thereby allows for, for example, ameliorating a symptom of irritable bowel syndrome (IBS) and ameliorating or preventing obesity.

Therefore, the composition containing astaxanthin is useful as a pharmaceutical composition for ameliorating or preventing these symptoms.

DESCRIPTION OF EMBODIMENTS (1) Intestinal Bacterial Flora of a Rodent

Six-week-old Wistar rats (rodents) were used to compare the intestinal bacterial flora of a group fed with a diet containing 0.02% astaxanthin (an Asx group) and the intestinal bacterial flora of a group fed with a normal diet (a control group).

Saline or corticotropin-releasing hormone (CRH) was intravenously administered to the rats after feeding each group with each corresponding diet for four weeks.

Three hours after administration, the rats were sacrificed and the intestinal bacterial floras in the cecum contents of each group were analyzed and compared. The result is shown in the graph of FIG. 1.

The analysis method included extracting DNA in the cecum contents, amplifying the V3-V4 region in a 16SrRNA gene, and performing sequencing.

FIG. 1 shows that the bacterial strain that increased in the Asx group as compared with the control group was a bacterium of the genus *Akkermansia* and the number of the bacteria of the genus *Akkermansia* in the Asx group increased and was about 11.7 times higher than that of the control group.

The bacterial strain that decreased in the Asx group as compared with the control group was Clostridia (decreased from 58.2% to 47.6%) and *Lactobacillus* (decreased from 10.9% to 5.9%).

Furthermore, enhancement of intestinal peristaltic movement induced by administration of CRH was reduced in the Asx group.

Therefore, it is presumed that ingestion of the composition containing astaxanthin produces an effect of increasing the proportion of *Akkermansia muciniphila* belonging to the genus *Akkermansia* in the intestinal bacterial flora by a factor of about 10 or more.

(2) Body Weight of a Rodent

Twenty four-day-old Wistar rats (rodents) were used to compare the body weights of a group fed with a diet containing 0.02% astaxanthin (an Asx group) and the body weights of a group fed with a normal diet (a control group).

The table in FIG. 2(*a*) shows the postnatal day (PND), body weights, and variation in body weights of the rats (rodents). FIG. 2(*b*) shows an average body weight and an average increase of PND72,76.

The result shows that increase in body weight was clearly less in the Asx group.

Therefore, it is presumed that ingestion of the composition containing astaxanthin is effective for, for example, ameliorating a symptom of irritable bowel syndrome (IBS) and ameliorating or preventing obesity.

(3) An Astaxanthin Concentration in Rodent Blood

Next, an astaxanthin concentration in rodent blood was investigated.

In this context, a blood astaxanthin concentration means an astaxanthin concentration in blood serum or blood plasma.

A study was performed as follows: a mouse or a rat (a rodent) was fed with a diet containing 0.02% astaxanthin for about one month and blood was collected to obtain blood serum or blood plasma; and a blood astaxanthin concentration was measured by HPLC.

Analysis was performed as follows:
<Sample Treatment>

Five hundred microliters of 50 µg/ml butylhydroxytoluene in ethanol and 100 µl of 100 ng/ml internal standard (trans-β-Apo-8'-carotenal) in acetone were added to 100 µl of the obtained blood serum or blood plasma sample, and the mixture was stirred vigorously for 15 seconds by a vortex mixer.

Furthermore, 5 ml of hexane was added to the blood serum or blood plasma, and subsequently the mixture was stirred vigorously for 15 seconds by the vortex mixer three times and centrifuged at 3500 rpm for 10 minutes.

Four milliliters of the supernatant after centrifugation was collected and filtrated through a membrane filter with a mesh size of 0.45 µm.

This filtrate was concentrated by a centrifugal evaporator. Then, the concentrate was redissolved in 150 µl of acetone and was subjected to reverse-phase HPLC.

In parallel, a standard solution was prepared by adding 2.5 ml of 800 ng/ml internal standard in acetone to 1 ml of 2 µg/ml astaxanthin(astaxanthin, ALEXIS BIOCHEMICALS, 460-031-M250) in acetone and adding acetone to make 20 ml, and was also subjected to reverse-phase HPLC.

The blood astaxanthin concentration was calculated based on the peak area ratio of the above-mentioned two solutions obtained by HPLC.
<Hplc Conditions>

Shimadzu LC-20A series (pump: LC-20AD, degasser: DGU-20A5R, autosampler: SIL-20AC, column oven: CTO-20AC, detector: SPD-20AV, system controller: CBM-20A) were used for HPLC.

YMC-Carotenoid (4.6×250 mm, particle size: 5 µm) was used as an analytical column.

The mobile phase included methanol as solvent A, tert-butyl methyl ether as solvent B, and 1% aqueous phosphate solution as solvent C.

Gradient elusion was performed so that the mixing ratio of solvent A and solvent B was 81%:15% when flowing of the mobile phase was started, and the mixing percentage of solvent B became 30% at 15 minutes and 80% at 23 minutes. After maintaining the mixing percentage of solvent B at 80% until 27 minutes, the mixing ratio was returned to the starting mixing ratio at 27.1 minutes and this starting mixing ratio was maintained until 35 minutes.

The mixing percentage of solvent C was consistently maintained at 4%.

The temperature of the column oven was set at 25° C. and measurement was performed at a detection wavelength of 470 nm by using a UV/VIS detector.

The flow rate of the mobile phase was set at 1 ml/min.

Figure 3:
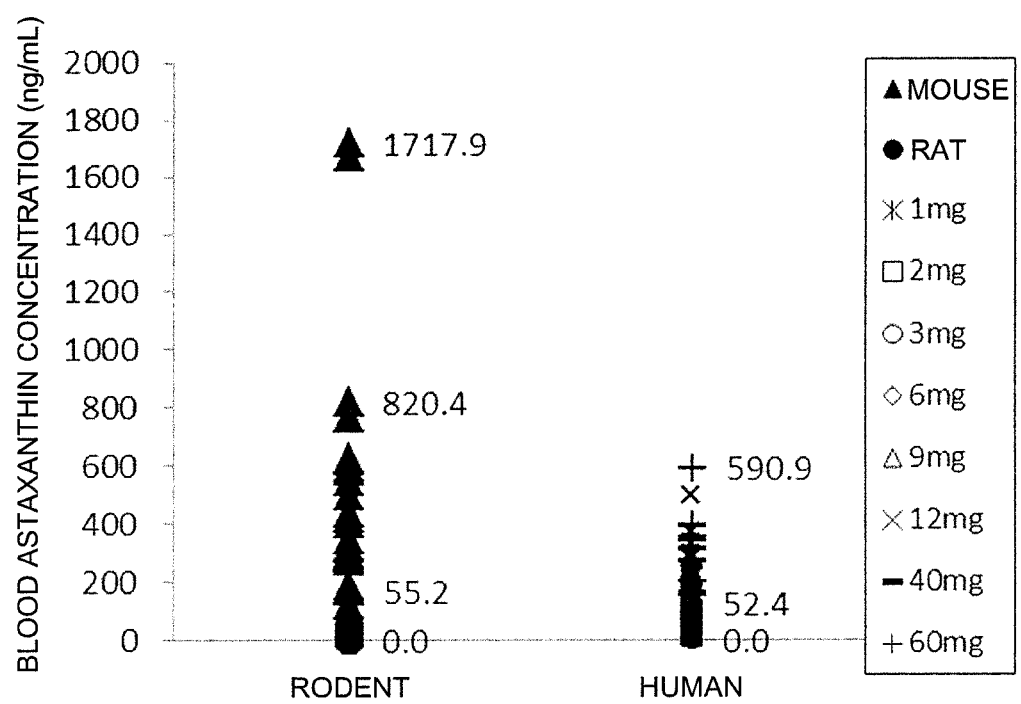
FIG. 3 shows comparison of blood astaxanthin concentrations between a rodent and a human.

The result of measurement of the astaxanthin concentration in rodent blood is shown in FIG. 3.

When the mouse or the rat was fed with the diet containing 0.02% astaxanthin for about one month, the range of the blood astaxanthin concentration was more than 0 and no more than 1720 ng/ml.

(4) Astaxanthin Concentration in Human Blood

Next, an astaxanthin concentration in human blood was investigated.

In this context, a blood astaxanthin concentration means an astaxanthin concentration in blood serum or blood plasma.

A blood astaxanthin concentration was measured by HPLC.

Analysis was performed as follows:
<Sample Treatment>

Five hundred microliters of 50 µg/ml butylhydroxytoluene in ethanol, 100 µl of 100 ng/ml internal standard (ethyl 8'-apo-beta-caroten-8'-oate, Carote Nature, 1010) in acetone, and 500 µl of distilled water were added to 100 µl of the obtained blood serum or blood plasma sample, and the mixture was stirred vigorously for 15 seconds by a vortex mixer.

Furthermore, 5 ml of hexane was added to the blood serum or blood plasma, and subsequently the mixture was stirred vigorously for 15 seconds by the vortex mixer three times and centrifuged at 3500 rpm for 10 minutes.

Four milliliters of the supernatant after centrifugation was collected and filtrated through a membrane filter with a mesh size of 0.45 µm.

This filtrate was concentrated by a centrifugal evaporator. Then, the concentrate was redissolved in 150 µl of acetone and was subjected to reverse-phase HPLC.

In parallel, a standard solution was prepared by adding 1 ml of 10 µg/ml internal standard (ethyl 8'-apo-beta-caroten- 8'-oate) in acetone to 100 ml of 100 ng/ml astaxanthin (astaxanthin, ALEXIS BIOCHEMICALS, 460-031-M250) in acetone, and was also subjected to reverse-phase HPLC. The blood astaxanthin concentration was calculated based on the peak area ratio of the above-mentioned two solutions obtained by HPLC.

<Hplc Conditions>

Shimadzu LC-20A series (pump: LC-20AD, degasser: DGU-20A5R, autosampler: SIL-20AC, column oven: CTO-20AC, detector: SPD-20AV, system controller: CBM-20A) were used for HPLC.

YMC-Carotenoid (4.6×250 mm, particle size: 5 µm) was used as an analytical column.

The mobile phase included methanol as solvent A, tert-butyl methyl ether as solvent B, and 1% aqueous phosphate solution as solvent C. Gradient elusion was performed so that the mixing ratio of solvent A and solvent B was 93%:5% when flowing of the mobile phase was started, and the mixing percentage of solvent B became 16% at 4 minutes, 22.5% at 7 minutes, 48.75% at 25.6 minutes, and 90% at 33.2 minutes. After maintaining the mixing percentage of solvent B at 90% until 41.5 minutes, the mixing ratio was returned to the starting mixing ratio at 41.7 minutes and this starting mixing ratio was maintained until 53.4 minutes.

The mixing percentage of solvent C was consistently maintained at 2%.

The temperature of the column oven was set at 16° C. and measurement was performed at a detection wavelength of 470 nm by using a UV/VIS detector.

The flow rate of the mobile phase was set at 1 ml/min.

The results of measurement of the astaxanthin concentration in rodent blood and human blood are shown in FIG. 3.

When a human received 1 to 60 mg of astaxanthin per day, the range of the blood astaxanthin concentration was more than 0 and no more than 600 ng/ml.

As the astaxanthin concentrations in rodent blood and human blood are found to be correlated to some extent, it is presumed that the above-mentioned effect of increasing *Akkermansia muciniphila* in a Wistar rat resulting from administration of astaxanthin is also observed in a human.

(5) Change in an Astaxanthin Concentration in Human Blood

Next, a test on humans was performed to monitor how an astaxanthin concentration in blood (in blood plasma) changed when astaxanthin was ingested for a long period. A study was performed as follows:

1. Subjects

Ten healthy Japanese males and females aged 20 years or older and younger than 50 years 2. Diet to be Tested and Ingestion of it The subjects ingested two capsules per day (equivalent to 12 mg/day astaxanthin in free form) together with water 30 minutes after breakfast for 42 days, with one capsule containing 60 mg of *Haematococcus* alga extract (equivalent to 6 mg of astaxanthin in free form) and 270 mg of edible oil and fat.

3. Blood Collection and Astaxanthin Quantification

Blood collection was performed 1, 6, 13, 20, 27, 34, and 42 days after the first ingestion of the capsules to obtain blood plasma. The blood astaxanthin concentration was measured by the above-mentioned analytical method (HPLC).

<Results>

Figures 4A, 4B:
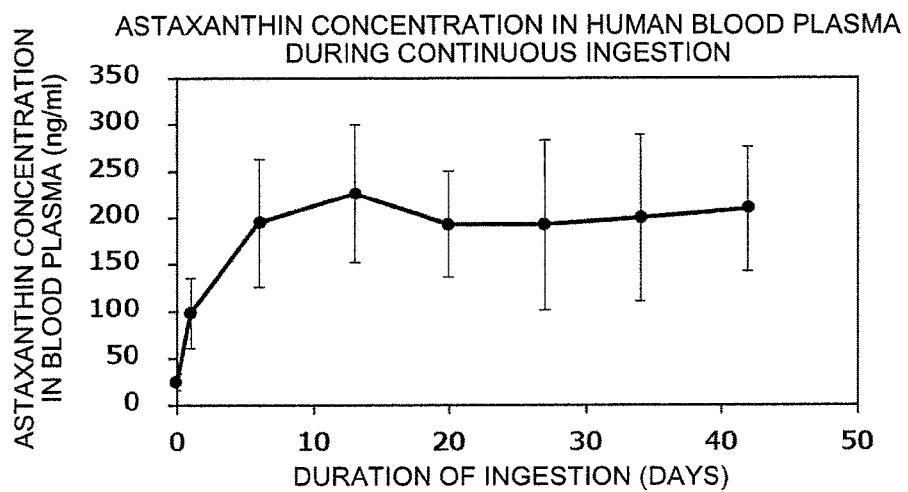
FIG. 4A shows the change in the astaxanthin concentration in human blood caused by continuous ingestion of astaxanthin.
FIG. 4B shows the measured data.

FIG. 4 shows the change in the astaxanthin concentration in human blood (in blood plasma) when astaxanthin was ingested for a long period.

As is shown in FIG. 4, when the subject consumed two units of food (capsules) per day for 42 days, with one unit containing 60 mg of *Haematococcus* alga extract (equivalent to 6 mg of astaxanthin in free form) and 270 mg of edible oil and fat, it was found that the astaxanthin concentration in human blood (in blood plasma) started to plateau around 200 ng/ml when about 6 days passed after the beginning of ingestion. These results revealed that the astaxanthin concentration in human blood (in blood plasma) did not decrease as long as the subject at least continued to consume the food containing astaxanthin.

INDUSTRIAL APPLICABILITY

The present invention is effective for increasing bacteria belonging to the genus *Akkermansia* in an intestinal bacterial flora and astaxanthin can be ingested in various methods. Increase of the bacteria (*muciniphila*) belonging to the genus *Akkermansia* in the intestinal bacterial flora can allow for, for example, ameliorating a symptom of irritable bowel syndrome (IBS) and ameliorating or preventing obesity. Therefore, the present invention is also useful in ingestion as a pharmaceutical composition.

Although only some embodiments of the present invention have been described in detail above, those skilled in the art will readily appreciate that many modifications are possible in the embodiments without materially departing from the novel teachings and advantages of this invention. Accordingly, all such modifications are intended to be included within scope of this invention.

What is claimed is:

1. A method of suppressing appetite or promoting weight loss in an obese patient, comprising administering a therapeutically effective amount of a composition comprising astaxanthin, wherein said administration increases a percentage of bacteria belonging to the genus *Akkermansia* and decreases a percentage of bacteria belonging to the genuses Clostridia and *Lactobacillus* in the intestinal bacterial flora of said patient, wherein the daily amount of astaxanthin administered is from 1 to 40 mg.

2. The method of claim 1, wherein said bacteria belonging to the genus *Akkermansia* are *Akkermansia muciniphila*.

3. The method of claim 1, wherein said composition containing astaxanthin is administered so that a blood astaxanthin concentration becomes more than 0 and no more than 600 ng/ml.

4. The method of claim 1, wherein said daily amount of said astaxanthin is 1 to 2 mg.

5. The method of claim 1, wherein said daily amount of said astaxanthin is 6 to 40 mg.

* * * * *